United States Patent [19]
Okuyama et al.

[11] Patent Number: 4,507,279
[45] Date of Patent: Mar. 26, 1985

[54] COSMETIC COMPOSITIONS OF THE OIL-IN-WATER EMULSION TYPE

[75] Inventors: Genichiro Okuyama; Shizume Takemoto; Yasuhisa Otani, all of Odawara, Japan

[73] Assignee: Kanebo, Ltd., Tokyo, Japan

[21] Appl. No.: 92,140

[22] Filed: Nov. 7, 1979

[30] Foreign Application Priority Data

Nov. 11, 1978 [JP] Japan .................... 53-139095

[51] Int. Cl.$^3$ ............... A61K 7/021; A61K 47/00
[52] U.S. Cl. ................... 424/63; 514/772; 514/776; 514/784
[58] Field of Search .................. 424/359, 365, 63

[56] References Cited

U.S. PATENT DOCUMENTS 4,115,548 9/1978 Marsh et al. .................. 424/365
4,183,917 1/1980 Iwao et al. .................... 424/365

FOREIGN PATENT DOCUMENTS 743882   6/1970  Belgium ..................... 424/359
2509255  9/1976  Fed. Rep. of Germany ...... 424/359
46-14355 4/1971  Japan ...................... 424/359
49-20340 2/1974  Japan ...................... 424/359
50-25741 3/1975  Japan ...................... 424/359
155637  12/1975  Japan ...................... 424/359

Primary Examiner—Dale R. Ore
Attorney, Agent, or Firm—Flynn, Thiel, Boutell & Tanis

[57] ABSTRACT

This invention relates to a cosmetic composition of the oil-in-water type comprising an oily substance having no free carboxyl group, water, and an emulsifier composed of either a combination of a basic polypeptide and a higher fatty acid or a salt (soap) formed from these compounds. This cosmetic composition using such an emulsifier derived from naturally occurring materials causes no irritation to the skin, as contrasted with cosmetic compositions using synthetic emulsifiers. In addition, it shows excellent emulsion stability and storage stability, gives an agreeable feeling, and presents an attractive appearance (fine texture and good gloss).

12 Claims, No Drawings

COSMETIC COMPOSITIONS OF THE OIL-IN-WATER EMULSION TYPE

BACKGROUND OF THE INVENTION (1) Field of the Invention

This invention relates to cosmetic compositions in which an oily substance is made into an oil-in-water emulsion (hereinafter referred to as an O/W emulsion) with the aid of an emulsifier composed of either a combination of a basic polypeptide and a higher fatty acid, both being compounds derived from naturally occurring materials, or a salt (soap) formed from these compounds. It also relates to cosmetic compositions of the O/W emulsion type which cause no irritation to the skin, have great safety and affinity for the skin, show excellent emulsion stability and storage stability, and present an attractive appearance (fine texture and good gloss).

(2) Description of the Prior Art

It is well known in the prior art that skin cosmetics of the emulsion type, such as creams and milky lotions, are required to satisfy the following conditions:

(1) They must cause no irritation to the skin and hence have great safety for the skin.
(2) They must have excellent emulsion stability and storage stability.
(3) They must have good chemical stability including high resistance to hydrolysis.
(4) They must present an attractive appearance from the viewpoints of texture and gloss.
(5) They must have great affinity for the skin.

In order to meet these requirements, elaborate compositional designs are being made, for example, by selection of suitable emulsifiers, search for useful combinations thereof, and concomitant use of special base materials. However, it is not easy to accomplish that purpose. Especially, it is very difficult to satisfy the above-described conditions by using a single emulsifier.

For example, nonionic surface active agents of the polyoxyethylene alkyl ether type are strongly irritative to the skin and poor in emulsifying power. Nonionic surface active agents of the ester type, such as polyoxyethylene fatty acid esters, polyoxyethylene glycerol fatty acid esters, polyoxyethylene sorbitan fatty acid esters, and the like, are poor in emulsifying power and resistance to hydrolysis.

Anionic surface active agents, such as sulfuric esters of higher alcohols, alkylarylsulfonic acid salts, and higher fatty acid salts, and the like, have a strong degreasing power and cause irritation to the skin.

Cationic surface active agents and ampholytic surface active agents are also irritative to the skin.

Meanwhile, soaps made from higher fatty acids are being commonly used as emulsifiers. Typical examples thereof include triethanolamine-stearic acid, sodium hydroxide (or potassium hydroxide)-stearic acid, and borax-beeswax soaps.

However, as is often mentioned in the literature, the triethanolamine-stearic acid soap used over a long period of time is allergenic to persons having a certain constitutional disposition. The sodium hydroxide (or potassium hydroxide)-stearic acid soap involves some operational problems (e.g., difficulty in pH adjustment) and has the disadvantage of being poor in emulsifying power (e.g., the resulting emulsion tends to be broken upon exposure to high temperatures). With the borax-beeswax soap, an excess of borax is liable to induce allergy.

The present inventors have made great efforts to search for soaps (emulsifiers) derived from natural materials and characterized by the properties of inducing no or little allergy, exerting a mild action on the skin, and providing stable emulsions, and have discovered that soaps (emulsifiers) made from a basic polypeptide and a higher fatty acid can provide very stable emulsions which cause no irritation to the skin and give an agreeable feeling. The present invention is based on this discovery.

SUMMARY OF THE INVENTION

It is an object of the present invention to provide a cosmetic composition of the O/W emulsion type which exerts a mild action on the skin without causing any irritation thereto, has great affinity for the skin, gives an agreeable feeling, shows excellent emulsion stability and storage stability, and presents an attractive appearance (fine texture and good gloss).

It is another object of the present invention to provide novel emulsifiers derived from naturally occurring materials.

These and other objects of the present invention can be accomplished by a cosmetic composition of the oil-in-water (O/W) emulsion type comprising (1)
  (a) a combination of from 0.5 to 10% by weight of a basic polypeptide having an average molecular weight of from 450 to 10,000 and an amino acid composition characterized by a basic amino acid-/acidic amino acid ratio of from 1.05 to 3.0 and an appropriate amount of a higher fatty acid containing from 12 to 22 carbon atoms, the higher fatty acid being used in an amount equal to from 0.2 to 30 times of the basic polypeptide, or
  (b) from 1.0 to 20% by weight of a salt formed from the basic polypeptide and the higher fatty acid in the proportion defined above;

(2) from 0.5 to 60% by weight of an oily substance having no free carboxyl group, the oily substance being selected from the group consisting of higher aliphatic hydrocarbons, animal or vegetable fats and oils, ester oils, waxes, higher alcohols, and combinations thereof; and (3) from 25 to 90% by weight of water.

DETAILED DESCRIPTION OF THE PREFERRED EMBODIMENTS

The basic polypeptide used in the cosmetic composition of the present invention can be prepared by any conventional procedure. By way of example, a naturally occurring protein (e.g., collagen, albumin, histone, or protamine) is partially hydrolyzed with a proteolytic enzyme (e.g., protease) or an acid (e.g., hydrochloric acid). The resulting hydrolyzate is passed through an ion exchange resin, on which only basic polypeptide components are adsorbed. Thereafter, the adsorbed basic polypeptide components are eluted with aqueous ammonia, concentrated, and then lyophilized. The average molecular weight of the basic polypeptide thus obtained can be regulated by controlling the hydrolysis time or by passing the eluate through a molecular sieve such as Sephadex.

The basic polypeptide used in the cosmetic composition of the present invention should have an average molecular weight of from 450 to 10,000 and preferably from 1,000 to 5,000. If the average molecular weight is less than 450, the resulting cosmetic composition tends to be poor in emulsion stability, storage stability, appearance, and the like, while if it is greater than 10,000, the resulting cosmetic composition tends to be poor in emulsion stability, storage stability, appearance, gloss, feeling, and the like.

Moreover, the basic polypeptide should have an amino acid composition characterized by a basic amino acid/acidic amino acid ratio of from 1.05 to 3.0 and preferably from 1.2 to 2.0. If the ratio is less than 1.05, the resulting cosmetic composition tends to be poor in emulsion stability, storage stability, appearance (texture and gloss), feeling, and the like, while if it is greater than 3.0, the resulting cosmetic composition tends to be poor in emulsion stability, storage stability, gloss, feeling, and the like.

Furthermore, the basic polypeptide should preferably have an isoelectric point of from 8.5 to 10.5 and more preferably from 9.0 to 10.0.

The basic polypeptide is used in an amount of from 0.5 to 10% by weight and preferably from 1.0 to 8.0% by weight based on the total weight of the cosmetic composition. If the amount of basic polypeptide used is less than 0.5% by weight, the resulting cosmetic composition tends to be poor in emulsion stability, storage stability, appearance, gloss, feeling, and the like, while if it is greater than 10% by weight, the resulting cosmetic composition tends to be poor in emulsion stability, storage stability, gloss, feeling, and the like.

The higher fatty acid used in the cosmetic composition of the present invention is selected from straight-chain or branched higher fatty acids containing from 12 to 22 carbon atoms. Hydroxyl-containing higher fatty acids may also be used. Specific examples of the higher fatty acid include lauric acid, myristic acid, palmitic acid, stearic acid, oleic acid, isostearic acid, isopalmitic acid, octyldecanoic acid, arachidonic acid, hydroxystearic acid, and the like. Among them, saturated fatty acids containing from 14 to 18 carbon atoms are preferred and specific examples thereof include myristic acid, palmitic acid, stearic acid, isopalmitic acid, isostearic acid, and the like.

The higher fatty acid containing from 12 to 22 carbon atoms is used in an amount equal to from 0.2 to 30 times and preferably 0.5 to 15 times the amount of basic polypeptide used (i.e., from 0.5 to 10% by weight based on the total weight of the cosmetic composition). If the amount of higher fatty acid used is less than 0.2 time the amount of basic polypeptide used, the resulting cosmetic composition is markedly poor in emulsion stability, storage stability, appearance, gloss, and feeling, while if it is greater than 30 times the amount of basic polypeptide used, the resulting cosmetic composition is poor in emulsion stability and appearance (texture and gloss) and feels greasy.

The above-defined amounts of basic polypeptide and higher fatty acid used apply to the embodiment in which an oily substance and water are made into an O/W emulsion by using those compounds in the free state.

In accordance with an alternative embodiment of the present invention, a salt (which can also be regarded as a soap) formed from the above-described basic polypeptide and higher fatty acid is used as emulsifier. Such a salt can readily be prepared, for example, by melting the higher fatty acid and mixing the resulting melt homogeneously with an aqueous solution (heated at a temperature of from 50° to 80° C.) of the basic polypeptide. Under these conditions, the basic polypeptide readily reacts with the higher fatty acid in the presence of water (reaction medium), resulting in the formation of a salt (or soap). Depending on the basic polypeptide concentration of the aqueous solution used in this salt-forming reaction, the hydrous salt thus obtained takes the form of a liquid, paste, or solid.

In the preparation of the above-described salt, the higher fatty acid is used in an amount equal to from 0.2 to 30 times and preferably from 0.5 to 5 times the weight of basic polypeptide used. If the amount of higher fatty acid used is less than 0.2 time the weight of basic polypeptide used, the resulting salt (or soap) is so low in emulsifying power that the cosmetic compositions prepared therewith are undesirably poor in emulsion stability, storage stability, feeling, and the like, while if it is greater than 30 times the weight of basic polypeptide used, the resulting salt (or soap) is so low in water solubility and emulsifying power that the cosmetic compositions prepared therewith are undesirably poor in emulsion stability and storage stability and feel greasy.

A preferred salt (or soap) is obtained by melting the higher fatty acid (for example, by heating it to a temperature of from 50° to 80° C.) and mixing the resulting melt with an aqueous solution (heated at a temperature of from 50° to 80° C.) containing 1 part by weight of the basic polypeptide in from 1 to 10 parts. The salt (in anhydrous form) thus obtained is usually soluble in water, sparingly soluble in ethyl alcohol, and insoluble in acetone, benzene, petroleum ether, and the like.

In the cosmetic composition of the present invention, the salt formed from the basic polypeptide and the higher fatty acid is used in an amount of from 1 to 20% by weight and preferably from 2 to 15% by weight based on the total weight of the cosmetic composition. If the amount of salt used is less than 1% by weight, the resulting cosmetic composition is poor in emulsion stability, storage stability, appearance, and the like and feels rough, while if it is greater than 20% by weight, the resulting cosmetic composition is poor in emulsion stability, storage stability, appearance, and the like and feels sticky.

The oily substance used in the cosmetic composition of the present invention, which should have no free carboxyl group, is selected from the group consisting of higher aliphatic hydrocarbons, animal or vegetable fats and oils, ester oils, waxes, higher alcohols, and combinations thereof. Specific examples of the higher aliphatic hydrocarbons include liquid paraffin, squalane, vaseline, ceresin, and the like. Specific examples of the animal or vegetable fats and oils include olive oil, almond oil, avocado oil, castor oil, cocoa butter, palm oil, turtle oil, cod-liver oil, whale oil, beef tallow, butter fat, and the like. Specific examples of the ester oils include isopropyl myristate, isopropyl palmitate, butyl stearate, hexyl laurate, octyldodecyl myristate, di-isopropyl adipate, isocetyl myristate, di-isopropyl sebacate, and the like. Specific examples of the waxes include beeswax, carnauba wax, spermaceti, lanolin, wool wax, solid paraffin, and the like. Specific examples of the higher alcohols include cetyl alcohol, oleyl alcohol, isostearyl alcohol, and the like. The above-described oily substances may be used alone or in combination.

In the cosmetic composition of the present invention, the oily substance having no free carboxyl group is used in an amount of from 0.5 to 60% by weight and preferably from 2 to 30% by weight based on the total weight of the cosmetic composition. If the amount of oily substance used is less than 0.5% by weight or greater than 60% by weight, the resulting cosmetic composition is poor in emulsion stability, feeling, appearance, and gloss.

In the cosmetic composition of the present invention, water is used in an amount of from 25 to 90% by weight and preferably from 30 to 80% by weight based on the total weight of the cosmetic composition.

Where the cosmetic composition of the present invention is adapted for use as a massage cream, cleansing cream, skin cream, skin milk, or the like, no pigment need be incorporated thereinto. However, where it is adapted for use as a foundation cream or liquid makeup base, at least one pigment must be incorporated thereinto, along with the above-described ingredients. In this case, the pigment is used in an amount of not greater than 10% by weight and preferably from 0.5 to 7% by weight based on the total weight of the cosmetic composition. Specific examples of the pigment include titanium dioxide, kaolin, yellow iron oxide, tri-iron tetroxide, talc, and the like.

If desired, the cosmetic composition of the present invention can further contain small amounts of cosmetically and pharmacologically active substances, perfumes, preservatives, colorants, wetting agents, and the like.

The cosmetic composition of the present invention can be prepared by any conventional procedure. By way of example, where it is desired to use an emulsifier composed of a combination the above-described basic polypeptide and higher fatty acid in the free state, a mixture of oily-phase ingredients including the oily substance and the higher fatty acid is melted by heating it to a temperature of from 75° to 85° C., and an aqueous solution (heated at a temperature of from 75° to 85° C.) containing the basic polypeptide, a preservative, and the like is added thereto. The resulting mixture is emulsified by homogenizing it in a homomixer or the like, and then cooled under agitation. When its temperature reaches 30° C., a perfume is mixed therein to obtain a final product. (If it is desired to incorporate one or more pigments thereinto, they should be dispersed in the above-described aqueous solution).

Alternatively, where it is desired to use an emulsifier composed of a salt formed from the above-described basic polypeptide and higher fatty acid, the oily substance is melted by heating it to a temperature of from 75° to 85° C., and an aqueous solution (heated at a temperature of from 75° to 85° C.) containing the salt, a preservative, and the like is added thereto. The resulting mixture is emulsified by homogenizing it in a homomixer or the like, and then cooled. Then, a perfume is mixed therein to obtain a final product.

In either case, the resulting cosmetic composition consists of an O/W emulsion in which the basic polypeptide and higher fatty acid used in the free state or in the form of a salt are dissociated into polypeptide and higher fatty acid ions. The type of the emulsion can be determined by a number of conventional testing methods including the conductometric method (based on the fact that an O/W emulsion has electrical conductivity because its continuous phase is water), the coloring method (which comprises sprinkling the emulsion with a powder of a water-insoluble dye such as Sudan II or the like and seeing whether its continuous phase is colored), and the like. In this emulsion, the oily substance dispersed in water takes the form of fine and uniform droplets which are protected and stabilized by the polypeptide ions and the like.

The presence of the above-described salt (or soap) in the cosmetic composition of the present invention is confirmed in the following manner: A sample of the cosmetic composition is evaporated at low temperature to remove water completely, and the residue is dispersed in water. The resulting dispersion is acidified with hydrochloric acid or the like and extracted with ether and then with water. The presence of stearic acid in the ether extract can be demonstrated by gas chromatography, and the presence of polypeptide in the water extract by the ninhydrin reaction.

Owing to the above-described form of the emulsion, the cosmetic composition of the present invention presents a beautiful and attractive appearance characterized by a fine texture and a good gloss and, moreover, shows excellent emulsion stability and storage stability.

The emulsifier of the present invention, which is composed of either a combination of a basic polypeptide and a higher fatty acid or a salt formed from these compounds causes no irritation to the skin, exerts a mild action on the skin, and hence has great safety. Therefore, the cosmetic composition of the present invention does not pose the problem of skin irritation, as contrasted with cosmetic compositions using synthetic emulsifiers.

The cosmetic compositions of the O/W emulsion type which are within the scope of the present invention have great utility as massage creams, cleansing creams, skin creams, skin milks, cleansing milks, foundation creams, or liquid makeup bases and can thus produce outstanding cosmetic effects.

A basic polypeptide and a basic polypeptide-higher fatty acid salt, along with several conventional emulsifiers, were tested for irritativity to the skin. The substances tested include a basic polypeptide (No. 1), a basic polypeptide-higher fatty acid salt (No. 2), sodium stearate (No. 3), triethanolamine (No. 4), L-lysine (No. 5), L-arginine (No. 6), sodium lauryl sulfate (No. 7), polyoxyethylene (10EO) stearyl ether (No. 8), and polyoxyethylene (20EO) sorbitan monooleate (No. 9). Using a 5% aqueous solution of each substance, animal skin irritation tests were carried out according to the Draize technique which will hereinafter be described in detail. The results thus obtained are as follows:

| Substance Tested | Animal Skin Irritation Score |
|---|---|
| No. 1 | 0 |
| No. 2 | 0 |
| No. 3 | 0.3 |
| No. 4 | 0.3 |
| No. 5 | 0.1 |
| No. 6 | 0.6 |
| No. 7 | 2.0 |
| No. 8 | 0.8 |
| No. 9 | 1.1 |

It can be seen from these data that the basic polypeptide and the basic polypeptide-higher fatty acid salt cause no irritation to the skin.

The present invention is further illustrated by the following examples. In these examples, all parts and percentages are by weight.

The average molecular weights of basic polypeptides were determined by gel filtration using Sephadex, and the isoelectric points thereof by electrophoresis.

The gloss of the resulting emulsions was measured according to the method 2 described in JIS Z8741-1962 (Methods for Gloss Measurement).

The storage stability of the resulting emulsions was tested by placing their samples in a thermostatic chamber at 5° or 45° C. and allowing them to stand for 3 months. The testing conditions are indicated in the respective tables.

The appearance and feeling of the resulting emulsions were evaluated by 10 skilled examiners. The feeling was rated on the following basis:

| | |
|---|---|
| Very good | When the sample felt very smooth, very nongreasy, and very rich. |
| Good | When the sample felt fairly smooth, fairly nongreasy, and fairly rich. |
| Rather poor | When the sample felt rather rough, rather sticky, rather greasy, and rather watery. |
| Poor | When the sample felt very rough, very sticky, very greasy, and very watery. |

The irritativity of the resulting emulsion was examined by the following animal skin and human skin irritation tests.

(Animal Skin Irritation Tests)

(i) Testing Procedure

According to the Draize technique, three albino rabbits weighing 2,500–3,500 gm were employed. Hair on the back was clipped and 0.5 ml each of test samples were held in contact with the skin by means of a rubber sleeve.

Each animal with patches applied thereto was immobilized in an animal holder and its entire trunk was then wrapped with a rubber cloth. After 24 hours' exposure, the patches were removed and the resulting reactions were evaluated on the basis of the criteria given below. Readings were also taken after 72 hours, and the final scores represent the average values of the 24- and 72-hour readings.

(ii) Evaluation of Skin Reaction

| (1) Erythema and Eschar Formation | |
|---|---|
| No erythema | 0 |
| Very slight erythema | 1 |
| Well-defined erythema | 2 |
| Moderate to severe erythema | 3 |
| Severe erythema to slight eschar | 4 |
| (Total possible erythema score 4) | |
| (2) Edema Formation | |
| No edema | 0 |
| Very slight edema | 1 |
| Slight edema | 2 |
| Moderate edema | 3 |
| Severe edema | 4 |
| (Total possible edema score 4) | |

(iii) Evaluation of Irritant Properties

The average scores thus obtained were interpreted on the basis of following criteria:

| | |
|---|---|
| Less than 2 | Only mild irritation |
| From 2 to 5 | Moderate irritation |
| 6 and above | Severe irritation |

(Human Skin Irritation Tests)

(i) Testing Procedure

Randomly selected 25 male and 25 female subjects were employed. According to the closed patch test procedure, test samples were applied to the inside of the upper arm or forearm and covered with a bandage. After 24 hours, the patches were removed and the readings of reaction were rated on the basis of the criteria given below. Readings were also taken after 48 hours.

(ii) Rating

| | |
|---|---|
| Negative reaction | (−) |
| Doubtful reaction (faint erythema) | (−?) |
| Weakly positive reaction | (+) |
| Strongly positive reaction | (++) |
| Extremely positive reaction | (+++) |

(iii) Evaluation of Patch-test Reactions

The degree of irritation was evaluated on the basis of the percentage of positive cases rated as (+) or (++) or (+++).

EXAMPLE 1

Three O/W emulsions having the respective compositions indicated in Table 1 were prepared as follows: A mixture of liquid paraffin and oleic acid was heated to 65° C., and an aqueous solution of the respective basic substance in deionized water at 65° C. was added thereto. The resulting mixture was agitated at a rotational speed of 3,000 rpm in a homomixer and then cooled to 30° C. Thereafter, the emulsion so formed was allowed to stand at room temperature, and the occurence of its separation was judged by seeing whether the lowermost tenth part thereof became clear or not.

TABLE 1

| | | Run Number | | |
|---|---|---|---|---|
| Ingredient | | No. 1 (Test Run) | No. 2 (Control Run) | No. 3 (Control Run) |
| Liquid paraffin (parts) | | 30.0 | 30.0 | 30.0 |
| Oleic acid (parts) | | 3.0 | 3.0 | 3.0 |
| Basic Substance | Triethanolamine (parts) | — | 1.5 | — |
| | Basic Polypeptide (parts)* | 6.0 | — | — |
| Deionized Water (parts) | | 61.0 | 52.5 | 67.0 |

*This basic polypeptide was obtained by partially hydrolyzing egg albumin with hydrochloric acid, neutralizing and desalting the hydrolyzate, and then passing it through an ion exchange resin to collect basic polypeptide components. It had an isoelectric point of 8.5 and an average molecular weight of 700.

The stability of the emulsions thus obtained was evaluated as described above, and the results of evaluation are summarized in Table 2.

As can be seen from the data given in Table 2, the O/W emulsion (No. 1) prepared with a basic polypeptide of the present invention was more stable than the one (No. 2) prepared with triethanolamine.

TABLE 2

| Run Number<br>Time Elapsed | No. 1<br>(Test Run) | No. 2<br>(Control Run) | No. 3<br>(Control Run) |
|---|---|---|---|
| 0 hour | Good (stable) | Good (stable) | Separation |
| 1 hour | " | " | " |
| 6 hours | " | Separation | " |
| 12 hours | " | " | " |
| 24 hours | " | " | " |
| 3 months | " | " | " |

EXAMPLE 2

A series of O/W emulsions having the respective compositions indicated in Table 3 were prepared as follows: A mixture of oily-phase ingredients was melted by heating it to 80° C., and an aqueous solution containing aqueous-phase ingredients was heated to 80° C. and added thereto. The resulting mixture was emulsified by agitating it in a homomixer, and then cooled to 30° C. As a result, the skin creams of the O/W emulsion type were obtained. The properties of the polypeptides used in this example are summarized in Table 4.

TABLE 3

| | Ingredients | No. 4 (Test Run) | No. 5 (Test Run) | No. 6 (Control Run) | No. 7 (Control Run) | No. 8 (Control Run) | No. 9 (control Run) | No. 10 (Test Run) | No. 11 (Test Run) | No. 12 (Control Run) | No. 13 (Control Run) |
|---|---|---|---|---|---|---|---|---|---|---|---|
| Oily Phase | Cetyl Palmitate (parts) | 2.0 | 2.0 | 2.0 | 2.0 | 2.0 | 2.0 | 2.0 | 2.0 | 2.0 | 2.0 |
| | Cetanol (parts) | 2.5 | 2.5 | 2.5 | 2.5 | 2.5 | 2.5 | 2.5 | 2.5 | 2.5 | 2.5 |
| | Liquid Paraffin (parts) | 8.0 | 8.0 | 8.0 | 8.0 | 8.0 | 8.0 | 8.0 | 8.0 | 8.0 | 8.0 |
| | Vaseline (parts) | 3.0 | 3.0 | 3.0 | 3.0 | 3.0 | 3.0 | 3.0 | 3.0 | 3.0 | 3.0 |
| | Stearic Acid (parts) | 8.0 | 8.0 | 8.0 | 8.0 | 8.0 | 8.0 | 8.0 | 8.0 | 8.0 | 8.0 |
| Aqueous Phase | Propylene Glycol (parts) | 10.0 | 10.0 | 10.0 | 10.0 | 10.0 | 10.0 | 10.0 | 10.0 | 10.0 | 10.0 |
| | Deionized Water (parts) | 61.5 | 61.5 | 61.5 | 61.5 | 61.5 | 61.5 | 61.5 | 615. | 61.5 | 61.5 |
| | Methyl p-Hydroxy-bebzoate | Small amount | Small amount | Small amount | Small amount | Small amount | Small amount | Small amount | Small amount | Small amount | Small amount |
| | Basic Polypeptide I (parts) | 5.0 | — | — | — | — | — | — | — | — | — |
| | Basic Polypeptide II (parts) | — | 5.0 | — | — | — | — | — | — | — | — |
| | Neutral Polypeptide I (parts) | — | — | 5.0 | — | — | — | — | — | — | — |
| | Neutral Polypeptide II (parts)* | — | — | — | 5.0 | — | — | — | — | — | — |
| | Acidic Polypeptide I (parts) | — | — | — | — | 5.0 | — | — | — | — | — |
| | Acidic Polypeptide II (parts)** | — | — | — | — | — | 5.0 | — | — | — | — |
| | Basic Polypeptide III (parts) | — | — | — | — | — | — | 5.0 | — | — | — |
| | Basic Polypeptide IV (parts) | — | — | — | — | — | — | — | 5.0 | — | — |
| | Basic Polypeptide V (parts) | — | — | — | — | — | — | — | — | 5.0 | — |
| | Basic Polypeptide VI (parts) | — | — | — | — | — | — | — | — | — | 5.0 |

*The neutral polypeptide II was obtained by adding sodium hydroxide to the neutral polypeptide I until its pH reached 9.0.
**The acidic polypeptide II was obtained by adding sodium hydroxide to the acidic polypeptide I until its pH reached 9.0.

TABLE 4

| | Type of Polypeptide | | | | | | | |
|---|---|---|---|---|---|---|---|---|
| Properties | Basic Polypeptide I | Basic Polypeptide II | Neutral Polypeptide I | Acidic Polypeptide I | Basic Polypeptide III | Basic Polypeptide IV | Basic Polypeptide V | Basic Polypeptide VI |
| Starting Protein | Collagen | Histone | Collagen | Collagen | Histone | Histone | Collagen | Histone |
| Molecular Weight | 1,000 | 1,000 | 1,000 | 1,000 | 1,000 | 1,000 | 1,000 | 1,000 |
| Isoelectric Point | 8.5 | 8.7 | 7.4 | 4.7 | 8.7 | 9.0 | 8.4 | 9.1 |
| Amino Acid Composition (%) | | | | | | | | |
| Aspartic Acid | 4.0 | 4.1 | 4.8 | 7.1 | 5.1 | 4.3 | 4.5 | 3.3 |
| Glutamic Acid | 4.2 | 3.9 | 5.7 | 7.6 | 7.0 | 4.7 | 4.3 | 4.2 |
| Lysine | 3.1 | 3.4 | 2.8 | 2.5 | 8.7 | 11.6 | 3.0 | 11.3 |
| Histidine | 0.8 | 0.6 | 0.4 | 0.4 | 5.2 | 3.8 | 1.2 | 4.0 |
| Arginine | 3.7 | 4.9 | 3.3 | 2.1 | 10.1 | 11.4 | 3.7 | 11.0 |
| Ornithine | 1.0 | 0.7 | 0.6 | 0.4 | 0.2 | 0.3 | 1.1 | 0.1 |
| Isoleucine | 1.4 | 1.5 | 1.2 | 1.4 | 3.8 | 4.0 | 1.7 | 4.1 |
| Leucine | 2.1 | 2.7 | 2.3 | 2.9 | 7.8 | 8.0 | 2.5 | 8.2 |
| Proline | 15.2 | 13.1 | 12.2 | 12.0 | 2.7 | 2.6 | 14.0 | 2.5 |
| Hydroxyproline | 11.7 | 12.3 | 11.2 | 11.5 | 0.1 | 0.1 | 12.0 | 0.1 |
| Threonine | 1.4 | 1.5 | 1.7 | 1.5 | 6.0 | 6.4 | 1.1 | 6.2 |
| Serine | 1.3 | 1.8 | 3.0 | 2.3 | 5.2 | 5.0 | 1.4 | 4.9 |
| Glycine | 32.8 | 33.3 | 34.8 | 33.2 | 8.3 | 8.7 | 35.1 | 9.1 |
| Alanine | 12.2 | 11.0 | 12.2 | 10.9 | 9.5 | 10.2 | 10.3 | 10.3 |

TABLE 4-continued

| Properties | Type of Polypeptide | | | | | | | |
|---|---|---|---|---|---|---|---|---|
| | Basic Polypeptide I | Basic Polypeptide II | Neutral Polypeptide I | Acidic Polypeptide I | Basic Polypeptide III | Basic Polypeptide IV | Basic Polypeptide V | Basic Polypeptide VI |
| Others | 5.1 | 5.2 | 3.8 | 4.2 | 20.3 | 18.9 | 4.1 | 20.7 |
| Basic Amino Acid/Acidic Amino Acid Ratio | 8.6/8.2 = 1.05 | 9.6/8.0 = 1.2 | 7.1/10.5 = 0.68 | 5.4/14.7 = 0.37 | 24.2/12.1 = 2.0 | 27.1/9.0 = 3.0 | 9.0/8.8 = 1.02 | 26.4/7.5 = 3.52 |

The stability and appearance of the skin creams thus obtained were evaluated, and the results of evaluation are summarized in Table 5.

were used. As a result, seven skin creams of the O/W emulsion type were obtained.

The emulsion stability and storage stability of these

TABLE 5

| Properties | | Run Number | | | | | | | | | |
|---|---|---|---|---|---|---|---|---|---|---|---|
| | | No. 4 (Test Run) | No. 5 (Test Run) | No. 6 (Control Run) | No. 7 (Control Run) | No. 8 (Control Run) | No. 9 (Control Run) | No. 10 (Test Run) | No. 11 (Test Run) | No. 12 (Control Run) | No. 13 (Control Run) |
| Emulsion Stability (immediately after preparation) | | Good | Very good | Rather poor | Good | Separation | Rather poor | Very good | Good | Rather poor | Rather poor |
| Storage stability | 5° C., 3 months | Good | Very good | Rather poor | Good | Separation | Rather poor | Very good | Good | Rather poor | Rather poor |
| | 45° C., 3 months | Good | Very good | Separation | Rather poor | Separation | Rather poor | Very good | Good | Separation | Slight Separation |
| Appearance | Texture | Fine and good | Fine and good | Slightly coarse | Fine | No emulsification | Slightly coarse | Fine and good | Fine and good | Coarse | Slightly coarse |
| | Gloss | Good | Good | | | | | Good | Good | Poor | Poor |
| Feeling | | Good (non-greasy) | Very good (non-greasy) | Poor | Poor | — | Poor | Very good (non-greasy) | Good (non-greasy) | Poor | Rather poor |
| Gloss Value | | 81 | 84 | 67 | 72 | — | 69 | 84 | 82 | 73 | 71 |

As can be seen from the data given in Table 5, the skin creams (Run Nos. 4, 5, 10, and 11) prepared with basic polypeptides of the present invention showed excellent emulsion stability and storage stability. Among these skin creams, those of Run Nos. 5 and 10 had a finer texture and a better gloss than those of Run Nos. 4 and 11.

In contrast, a neutral and an acidic polypeptide failed to provide a stable skin cream (Run Nos. 6 and 8). No significant improvement in emulsion stability or storage stability was noted even when these polypeptides were alkalified with sodium hydroxide to pH 9.0 (Run Nos. 7 and 9).

EXAMPLE 3

The procedure of Example 2 was repeated except that a variety of basic polypeptides having the respective average molecular weights indicated in Table 6 were used.

skin creams were evaluated, and the result of evaluation are summarized in Table 6.

It can be seen from the data given in Table 6 that, when lysine having a molecular weight of 146 was used (this amino acid can be regarded as a basic polypeptide having a degree of polymerization of 1), the resulting skin cream showed good emulsion stability but became markedly discolored and malodorous after storage (Run No. 14). In contrast, when basic polypeptide having average molecular weights of from 450 to 10,000 were used according to the present invention, the resulting skin creams showed good emulsion stability and underwent no appreciable changes after storage (Run Nos. 15, 16, 17, and 18). These properties were very good especially when the average molecular weight of the basic polypeptide was 1,000 or 5,000 (Run Nos. 16 and 17).

TABLE 6

| Properties | | Run Number | | | | | | |
|---|---|---|---|---|---|---|---|---|
| | | No. 14 (Control Run) | No. 15 (Test Run) | No. 16 (Test Run) | No. 17 (Test Run) | No. 18 (Test Run) | No. 19 (Control Run) | No. 20 (Control Run) |
| Average Molecular Weight of Basic Polypeptide Used | | 146 (lysine) | 450 | 1,000 | 5,000 | 10,000 | 20,000 | 400 |
| Emulsion Stability (immediately after preparation) | | Good | Good | Very good | Very good | Good | Rather poor | Rather poor |
| Storage Stability | 45° C., 3 months | Discolored and malodorous | Good | Very good | Very good | Good | Slight gelation | Rather poor (discolored) |
| | 5° C., 3 months | Good | Good | Very good | Very good | Good | Slight gelation | Rather poor |
| Appearance | | Good | Good | Very good | Very good | Good | Rather poor | Rather poor |
| Gloss | | Poor | Good | Good | Good | Good | Poor | Rather poor |
| Gloss Value | | 78 | 82 | 86 | 86 | 81 | 68 | 72 |

TABLE 6-continued

| | Run Number | | | | | | |
|---|---|---|---|---|---|---|---|
| Properties | No. 14 (Control Run) | No. 15 (Test Run) | No. 16 (Test Run) | No. 17 (Test Run) | No. 18 (Test Run) | No. 19 (Control Run) | No. 20 (Control Run) |
| Feeling | Nongreasy | Nongreasy | Nongreasy | Nongreasy | Nongreasy | Greasy | Nongreasy |

EXAMPLE 4

The procedure of Example 2 was repeated except that the basic polypeptide I described in Example 2 was used in the varying amounts indicated in Table 7. As a result, six skin creams of the O/W emulsion type were obtained.

The emulsion stability, appearance, and feeling of these skin creams were evaluated, and the results of evaluation are summarized in Table 7.

TABLE 7

| Run Number Ingredients and properties | | No. 21 (Control Run) | No. 22 (Test Run) | No. 23 (Test Run) | No. 24 (Test Run) | No. 25 (Test Run) | No. 26 (Control Run) |
|---|---|---|---|---|---|---|---|
| Oily Phase | Cetyl Palmitate (parts) | 2.5 | 2.5 | 2.5 | 2.5 | 2.5 | 2.5 |
| | Cetanol (parts) | 2.0 | 2.0 | 2.0 | 2.0 | 2.0 | 2.0 |
| | Liquid Paraffin (parts) | 8.0 | 8.0 | 8.0 | 8.0 | 8.0 | 8.0 |
| | Vaseline (parts) | 3.0 | 3.0 | 3.0 | 3.0 | 3.0 | 3.0 |
| | Stearic Acid (parts) | 8.0 | 8.0 | 8.0 | 8.0 | 8.0 | 8.0 |
| Aqueous Phase | Propylene Glycol (parts) | 10.0 | 10.0 | 10.0 | 10.0 | 10.0 | 10.0 |
| | Deionized Water (parts) | 66.4 | 66.0 | 65.5 | 58.5 | 56.5 | 46.5 |
| | Methyl p-Hydroxybenzoate | Small amount | Small amount | Small amount | Small amount | Small amount | Small amount |
| | Basic Polypeptide (parts) | 0.1 | 0.5 | 1.0 | 8.0 | 10.0 | 20.0 |
| Emulsion Stability (immediately after preparation) | | Fairly good | Good | Very good | Very good | Good | Good |
| Feeling | | Somewhat rough | Good | Very good | Very good | Good | Somewhat sticky |
| Storage Stability (45° C., 3 months) | | poor | Good | Very good | Very good | Good | Rather poor |
| Appearance (gloss) | | poor | Good | Very good | Very good | Good | Rather poor |

It can be seen from the data given in Table 7 that, when the amount of basic polypeptide used was from 0.5 to 10% by weight, the resulting skin creams showed good properties such as emulsion stability, appearance, and feeling (Run Nos. 22, 23, 24, and 25). These properties were very good especially when the amount of basic polypeptide used was 1 or 5% by weight (Run Nos. 23 and 24).

EXAMPLE 5

Using the respective basic substances indicated in Table 8, a series of O/W emulsions having an otherwise identical composition were prepared as follows: A mixture of oily-phase ingredients was melted by heating it to 80° C., and an aqueous solution containing aqueous-phase ingredient was heated to 80° C. and added thereto. The resulting mixture was emulsified by agitation and then cooled to 30° C. As a result, four skin milks of the O/W emulsion type were obtained. The basic polypeptide used in this example had an isoelectric point of 9.0 and an average molecular weight of 5,000.

TABLE 8

| Run Number Ingredients and Properties | | No. 28 (Test Run) | No. 29 (Control Run) | No. 30 (Control Run) | No. 31 (Control Run) |
|---|---|---|---|---|---|
| Oily Phase | Stearic Acid (Parts) | 3.0 | 3.0 | 3.0 | 3.0 |
| | Liquid Parrafin (parts) | 4.0 | 4.0 | 4.0 | 4.0 |
| | Cetanol (parts) | 2.0 | 2.0 | 2.0 | 2.0 |
| | Octyldodecyl Myristate (parts) | 2.0 | 2.0 | 2.0 | 2.0 |
| Aqueous Phase | Glycerol (parts) | 5.0 | 5.0 | 5.0 | 5.0 |
| | Methyl p-Hydroxybenzoate | Small amount | Small amount | Small amount | Small amount |
| | Deionized Water (parts) | 77.0 | 83.0 | 83.7 | 83.0 |
| | Basic Polypeptide (parts) | 7.0 | — | — | — |
| | Triethanolamine (parts) | — | 1.0 | — | — |
| | Potassium Hydroxide (parts) | — | — | 0.3 | — |
| | α-Lysine (parts) | — | — | — | 1.0 |
| Storage Stability (45° C. 3 months) | | Good | Slightly discolored | Slightly separated | Discolored and malodorous |
| Irrita- | Animal Skin | No | Slight | No | Slight |

TABLE 8-continued

| Run Number Ingredients and Properties | | No. 28 (Test Run) | No. 29 (Control Run) | No. 30 (Control Run) | No. 31 (Control Run) |
|---|---|---|---|---|---|
| tivity | Irritation Test | (0) | (2.3) | (0) | (1.8) |
| | Human Skin Irritation Test | No (0) | Slight (2.0) | No (0) | No. (0) |
| Feeling | | Non-greasy and good | Non-greasy and good | Non-greasy and good | Non-greasy and good |
| Appearance (gloss and texture) | | Very good | Good | Good | Good |
| Gloss Value | | 85 | 79 | 78 | 79 |

As can be seen from the data given in Table 8, the skin milk (Run No. 28) prepared with a basic polypeptide of the present invention underwent no appreciable changes after storage and caused no irritation to the animal and human skins. In contrast, the one (Run No. 29) prepared with triethanolamine became slightly discolored after storage and, moreover, caused slight irritation. The one (Run No. 30) prepared with potassium hydroxide became separated slightly after storage. The one (Run No. 31) prepared with lysine became discolored and malodorous after storage and, moreover, caused slight irritation.

EXAMPLE 6

A series of O/W emulsions having the respective compositions indicated in Table 9 were prepared. As a result, six hair creams of the O/W emulsion type were obtained. The basic polypeptide used in this example was the same as used in Example 5.

The stability, appearance, and feeling of these hair creams were evaluated, and the results of evaluation are summarized in Table 9.

TABLE 9

| Run Number Ingredients and Properties | | No. 32 (Test Run) | No. 33 (Test Run) | No. 34 (Test Run) | No. 35 (Test Run) | No. 36 (Test Run) | No. 37 (Test Run) |
|---|---|---|---|---|---|---|---|
| Oily Phase | Lauric Acid (parts) | 10.0 | — | — | — | — | — |
| | Myristic Acid (parts) | — | 10.0 | — | — | — | — |
| | Palmitic Acid (parts) | — | — | 10.0 | — | — | — |
| | Stearic Acid (parts) | — | — | — | 10.0 | — | — |
| | Isostearic Acid (parts) | — | — | — | — | 10.0 | — |
| | Oleic Acid (parts) | — | — | — | — | — | 10.0 |
| | Cetanol (parts) | 2.0 | 2.0 | 2.0 | 2.0 | 2.0 | 2.0 |
| | Glycerol Monostearate (parts) | 1.0 | 1.0 | 1.0 | 1.0 | 1.0 | 1.0 |
| | Squalane (parts) | 8.0 | 8.0 | 8.0 | 8.0 | 8.0 | 8.0 |
| Aqueous Phase | Basic Polypeptide (parts) | 8.0 | 8.0 | 8.0 | 8.0 | 8.0 | 8.0 |
| | Propylene Glycol (parts) | 5.0 | 5.0 | 5.0 | 5.0 | 5.0 | 5.0 |
| | Methyl p-Hydroxybenzoate | Small amount | Small amount | Small amount | Small amount | Small amount | Small amount |
| | Deionized Water (parts) | 66.0 | 66.0 | 66.0 | 66.0 | 66.0 | 66.0 |
| Emulsion Stability (immediately after preparation) | | Very good | Very good | Very good | Very good | Very good | Very good |
| Storage Stability (45° C., 3 months) | | Very good | Very good | Very good | Very good | Very good | Very good |
| Appearance (gloss and texture) | | Very good | Very good | Very good | Very good | Very good | Very good |
| Feeling | | Very good | Very good | Very good | Very good | Very good | Very good |

As can be seen from the data given in Table 9, all of the higher fatty acids used in this example provided useful hair creams (Run Nos. 32, 33, 34, 35, 36, and 37).

EXAMPLE 7

A series of O/W emulsions having the respective compositions indicated in Table 10 were prepared. The basic polypeptide used in this example was the same as used in Example 5.

TABLE 10

| Run Number Ingredients and Properties | | No. 38 (Control Run) | No. 39 (Test Run) | No. 40 (Test Run) | No. 41 (Test Run) | No. 42 (Test Run) | No. 43 (Test Run) |
|---|---|---|---|---|---|---|---|
| Oily phase | Mixture (parts) Consisting of | 0.5 | 1 | 8 | 28 | 60 | 63 |

TABLE 10-continued

| Run Number<br>Ingredients<br>and Properties | | No. 38<br>(Control<br>Run) | No. 39<br>(Test<br>Run) | No. 40<br>(Test<br>Run) | No. 41<br>(Test<br>Run) | No. 42<br>(Test<br>Run) | No. 43<br>(Test<br>Run) |
|---|---|---|---|---|---|---|---|
| | 20.0% Cetyl Palmitate<br>10.0% Cetanol<br>50.0% Liquid Paraffin<br>10.0% Vaseline<br>10.0% Ispropyl Palmitate | | | | | | |
| | Stearic Acid (parts) | 2.5 | 2.5 | 2.5 | 2.5 | 2.5 | 2.5 |
| Aqueous Phase | Xanthin Gum (part) | 0.3 | 0.3 | 0.3 | 0.3 | 0.3 | 0.3 |
| | Glycerol (parts) | 5.0 | 5.0 | 5.0 | 5.0 | 5.0 | 5.0 |
| | Methyl p-Hydroxy-benzoate | Small amount | Small amount | Small amount | Small amount | Small amount | Small amount |
| | Deionized Water (parts) | 89.7 | 89.2 | 82.2 | 62.2 | 30.2 | 27.2 |
| | Basic Polypeptide (parts) | 2.0 | 2.0 | 2.0 | 2.0 | 2.0 | 2.0 |
| Storage Stability (45° C., 3 months) | | Fairly good | Good | Very good | Very good | Good | Slight separation |
| Feeling | | Rather poor | Good | Very good | Very good | Good | Poor |
| Appearance (gloss and texture) | | Poor | Good | Very good | Very good | Good | Poor |

It can be seen from the data given in Table 10 that, when the amount of oily-phase ingredients was 1, 10, 30, or 60% by weight, the resulting milks or creams showed good properties (Run Nos. 39, 40, 41, and 42). These properties were very good especially when the amount of oily-phase ingredients was 10 or 30% by weight (Run Nos. 40 and 41).

EXAMPLE 3

A series of O/W emulsions having the respective compositions indicated in Table 11 were prepared. The basic polypeptide used in this example was the same as used in Example 5.

bility, appearance, and feeling (Run Nos. 45, 46, 47, 48, and 49).

EXAMPLE 9

Eight parts of a 30% aqueous solution of the basic polypeptide used in Example 5 was mixed with 1 part of stearic acid at 80° C. The resulting salt was in the form of a somewhat translucent paste. Two parts of liquid paraffin and 4 parts of water were added to this salt. The resulting mixture was heated to 80° C., emulsified by agitation, and then cooled to 30° C. As a result, a cream of the O/W emulsion type was obtained (Run No. 51).

TABLE 11

| Run Number<br>Ingredients<br>and Properties | | No. 44<br>(Control<br>Run) | No. 45<br>(Test<br>Run) | No. 46<br>(Test<br>Run) | No. 47<br>(Test<br>Run) | No. 48<br>(Test<br>Run) | No. 49<br>(Test<br>Run) | No. 50<br>(Control<br>Run) |
|---|---|---|---|---|---|---|---|---|
| Oily Phase | Beeswax (parts) | 1.5 | 1.5 | 1.5 | 1.5 | 1.5 | 1.5 | 1.5 |
| | Cetanol (parts) | 2.0 | 2.0 | 2.0 | 2.0 | 2.0 | 2.0 | 2.0 |
| | Liquid Paraffin (parts) | 4.0 | 4.0 | 4.0 | 4.0 | 4.0 | 4.0 | 4.0 |
| | Isopropyl Stearate (parts) | 2.0 | 2.0 | 2.0 | 2.0 | 2.0 | 2.0 | 2.0 |
| | Stearic Acid (parts) | 0.1 | 0.2 | 10 | 15 | 30 | 0.5 | 40 |
| Aqueous Phase | Deionized Water (parts) | 84.4 | 84.3 | 74.5 | 74.5 | 54.5 | 84.0 | 44.5 |
| | Glycerol (parts) | 5.0 | 5.0 | 5.0 | 5.0 | 5.0 | 5.0 | 5.0 |
| | Methyl p-Hydroxy-benzoate | Small amount | Small amount | Small amount | Small amount | Small amount | Small amount | Small amount |
| | Basic Polypeptide (part) | 1.0 | 1.0 | 1.0 | 1.0 | 1.0 | 1.0 | 1.0 |
| Emulsion Stability (immediately after preparation) | | Nearly good | Good | Very good | Very good | Good | Very good | Nearly good |
| Storage Stability (45° C., 3 months) | | Poor | Good | Very good | Very good | Good | Very good | Rather poor |
| Appearance (gloss and texture) | | Poor | Good | Very good | Very good | Good | Very good | Rather poor |
| Feeling | | Rather Poor | Good | Very good | Very good | Good | Very good | Greasy |

It can be seen from the data given in Table 11 that, when the ratio of higher fatty acid to basic polypeptide was from 0.2 to 30, the resulting emulsions showed good properties such as emulsion stability, storage sta- On the other hand, a mixture of 2 parts of liquid paraffin and 1 part of stearic acid was melted by heating it to 80° C. Another mixture of 4 parts of water and 8 parts of a 30% aqueous solution of the same basic polypeptide was heated to 80° C. and added to the above melt. The resulting mixture was emulsified by agitation and then cooled to 30° C. As a result, another cream of the O/W emulsion type was obtained (Run No. 52).

The properties of these creams are summarized in Table 12.

TABLE 12

| Run Number<br>Properties | No. 51<br>(Test Run) | No. 52<br>(Test Run) |
|---|---|---|
| Emulsion Stability (Immediately after preparation) | Very good (finely dispersed) | Very good (finely dispersed) |
| Storage Stability (room temperature, 3 months) | Very good | Very good |
| Appearance | Very Good | Very good |
| Gloss | Good | Good |
| Gloss Value | 86 | 86 |
| Feeling | Nongreasy and good | Nongreasy and good |

It can be seen from the data given in Table 12 that this combination of a basic polypeptide and a higher fatty acid provides a useful cream of the O/W emulsion type, whether they are used in the free state or in the form of a salt.

COMBINATION EXAMPLE 1

The procedure of Test Run No. 1 in Example 1 was repeated except that the basic polypeptide was replaced by the neutral polypeptide I of Example 2, the oleic acid was omitted, and the amount of water was increased to 64 parts. As a result, the ingredients virtually failed to form an emulsion and separated into two layers after 12 minutes.

COMPARATIVE EXAMPLE 2

The procedure of Test Run No. 1 in Example 1 was repeated except that the oleic acid was omitted and the amount of water was increased to 64 parts. As a result, the ingredients virtually failed to form an emulsion as in Comparative Example 1 and separated into two layers after 20 minutes.

EXAMPLE 10

Ten parts of each of the higher fatty acids indicated in Table 13 was melted by heating it to 80° C. This melt was mixed with an aqueous solution (at 80° C.) containing 8.0 parts of a basic polypeptide in 25 parts of water, and the resulting mixture was agitated to form a basic polypeptide-higher fatty acid salt. The properties of the salts thus obtained are summarized in Table 14.

TABLE 13

| | Run Number | | | | | |
|---|---|---|---|---|---|---|
| Ingredients | No. 53 (Test Run) | No. 54 (Test Run) | No. 55 (Test Run) | No. 56 (Test Run) | No. 57 (Test Run) | No. 58 (Test Run) |
| Lauric Acid (parts) | 8.0 | — | — | — | — | — |
| Myristic Acid (parts) | — | 8.0 | — | — | — | — |
| Palmitic Acid (parts) | — | — | 8.0 | — | — | — |
| Stearic Acid (parts) | — | — | — | 8.0 | — | — |
| Isostearic Acid (parts) | — | — | — | — | 8.0 | — |
| Oleic Acid (parts) | — | — | — | — | — | 8.0 |
| Water (parts) | 25.0 | 25.0 | 25.0 | 25.0 | 25.0 | 25.0 |
| Basic Polypeptide (parts) | 7.0 | 7.0 | 7.0 | 7.0 | 7.0 | 7.0 |

TABLE 14

| | Run Number | | | | | |
|---|---|---|---|---|---|---|
| Ingredients | No. 53 (Test Run) | No. 54 (Test Run) | No. 55 (Test Run) | No. 56 (Test Run) | No. 57 (Test Run) | No. 58 (Test Run) |
| Appearance | Yellowish-white solid paste | Yellowish-white solid paste | Yellowish-white solid paste | Yellowish-white solid paste | Yellowish-white paste | Yellowish-white paste |
| Miscibility with Water | Easily miscible with water | Easily miscible with water | Easily miscible with water | Easily miscible with water | Easily miscible with water | Easily miscible with water |
| pH | 7.5 | 7.4 | 7.2 | 7.3 | 7.2 | 7.3 |

Then, these salts were used to prepare a series of emulsions having the respective compositions indicated in Table 15. As can be seen from the data given in Table 15, the resulting emulsions were all useful as hair creams. All of them had an electric resistance of 10 kΩ or less and thus proved to be O/W emulsions.

TABLE 15

| Run Number<br>Ingredients and Properties | | No. 53 (Test Run) | No. 54 (Test Run) | No. 55 (Test Run) | No. 56 (Test Run) | No. 57 (Test Run) | No. 58 (Test Run) |
|---|---|---|---|---|---|---|---|
| Oily Phase | Cetanol (parts) | 2.0 | 2.0 | 2.0 | 2.0 | 2.0 | 2.0 |
| | Squalane (parts) | 8.0 | 8.0 | 8.0 | 8.0 | 8.0 | 8.0 |
| | Glyceral Monostearate (parts) | 1.0 | 1.0 | 1.0 | 1.0 | 1.0 | 1.0 |
| Aqueous Phase | Basic Polypeptide-Higher Fatty Acid Salt (parts)* | 40.0 | 40.0 | 40.0 | 40.0 | 40.0 | 40.0 |
| | Sorbitol | 5.0 | 5.0 | 5.0 | 5.0 | 5.0 | 5.0 |

TABLE 15-continued

| Run Number Ingredients and Properties | | No. 53 (Test Run) | No. 54 (Test Run) | No. 55 (Test Run) | No. 56 (Test Run) | No. 57 (Test Run) | No. 58 (Test Run) |
| --- | --- | --- | --- | --- | --- | --- | --- |
| | (parts) Methyl p-Hydroxy-benzoate | Small amount | Small amount | Small amount | Small amount | Small amount | Small amount |
| | Water (parts) | 44.0 | 44.0 | 44.0 | 44.0 | 44.0 | 44.0 |
| Emulsion Stability (immediately after preparation) | | Very good | Very good | Very good | Very good | Very good | Very good |
| Storage Stability (45° C., 3 months) | | Very good | Very good | Very good | Very good | Very good | Very good |
| Appearance | | Very good | Very good | Very good | Very good | Very good | Very good |
| Feeling | | Very good | Very good | Very good | Very good | Very good | Very good |

*The hydrous salt used in each run had a concentration of 15/40 × 100 = 37.5% and, therefore, the amount of the pure salt was 15 parts.

EXAMPLE 11

(Amount of Salt Used)

Sixty parts of stearic acid was melted and then mixed with an aqueous solution (at 80° C.) containing 40 parts of a basic polypeptide in 100 parts of water. The resulting salt was in the form of a hard paste. A series of emulsions were prepared by using this salt in the respective amounts indicated in Table 16. The basic polypeptide used in this example was the basic polypeptide III described in Example 2. The properties of the emulsions thus obtained are summarized in Table 16. All of them proved to be O/W emulsions as a result of measurement of their electric resistance.

should be from 1.0 to 20% by weight and preferably from 2.0 to 15% by weight based on the total weight of the cosmetic composition.

EXAMPLE 12

(Ratio of Higher Fatty Acid to Basic Polypeptide)

In the same manner as described in Example 11, various amounts of stearic acid were melted and then mixed with an aqueous solution at (80° C.) containing a fixed amount of a basic polypeptide. The resulting ratios of stearic acid to basic polypeptide are indicated in Table 17. The properties of the salts thus obtained are summarized in Table 17. The basic polypeptide used in this example was the basic polypeptide III described in Example 2.

TABLE 16

| Run Number Ingredients and Properties | | No. 59 (Control Run) | No. 60 (Test Run) | No. 61 (Test Run) | No. 62 (Test Run) | No. 63 (Test Run) | No. 64 (Control Run) |
| --- | --- | --- | --- | --- | --- | --- | --- |
| Oily Phase | Cetyl Palmitate (parts) | 2.0 | 2.0 | 2.0 | 2.0 | 2.0 | 2.0 |
| | Cetanol (parts) | 1.5 | 1.5 | 1.5 | 1.5 | 1.5 | 1.5 |
| | Liquid Paraffin (parts) | 8.0 | 8.0 | 8.0 | 8.0 | 8.0 | 8.0 |
| | Vaseline (parts) | 3.0 | 3.0 | 3.0 | 3.0 | 3.0 | 3.0 |
| Aqueous Phase | Basic Polypeptide-Stearic Acid Salt (parts)* | 1.0 (0.5) | 2.0 (1.0) | 4.0 (2.0) | 30.0 (15.0) | 40.0 (20.0) | 50.0 (25.0) |
| | Propylene Glycol (parts) | 10.0 | 10.0 | 10.0 | 10.0 | 10.0 | 10.0 |
| | Deionized Water (parts) | 74.5 | 73.5 | 71.5 | 45.5 | 35.5 | 25.5 |
| | Methyl p-Hydroxy-benzoate | Small amount | Small amount | Small amount | Small amount | Small amount | Small amount |
| Emulsion Stability (immediately after preparation) | | Rather poor | Good | Very good | Very good | Good | Rather poor |
| Storage Stability (45° C., 3 months) | | Rather poor | Good | Very good | Very good | Good | Rather poor |
| Feeling | | Somewhat rough | Good | Very good | Very good | Good | Somewhat sticky |
| Appearance (gloss and texture) | | Rather poor | Good | Very good | Very good | Good | Rather poor |

*The amounts of the hydrous salts, together with those of the pure salt in parentheses, are indicated.

As can be seen from the data given in Table 16, the amount of basic polypeptide-stearic acid salt used

TABLE 17

| Run Number Ingredients and Properties | No. 65 (Control Run) | No. 66 (Test Run) | No. 67 (Test Run) | No. 68 (Test Run) | No. 69 (Test Run) | No. 70 (Control Run) |
|---|---|---|---|---|---|---|
| Stearic Acid (parts)* | 0.03 (0.1) | 0.06 (0.2) | 0.15 (0.5) | 4.5 (15) | 9.0 (30) | 12.0 (40) |
| Basic Polypeptide (part) | 0.3 | 0.3 | 0.3 | 0.3 | 0.3 | 0.3 |
| Water (parts) | 2.0 | 2.0 | 2.0 | 2.0 | 2.0 | 2.0 |
| Appearance | Semi-liquid | Semi-liquid to paste | Paste | Paste | Hard paste | Solid powder |
| Miscibility with Water | Easily miscible | Easily miscible | Easily miscible | Somewhat cloudy | Partially immiscible | Fairly immiscible |
| pH | 8.7 | 8.6 | 8.4 | 7.5 | 7.2 | 6.9 |

*The ratios of stearic acid to basic polypeptide are indicated in parentheses.

Then, in the same manner as described in Example 11, a series of emulsions were prepared by using these salts in the respective amounts indicated in Table 18.

TABLE 18

| Run Number Ingredients and properties | | No. 65 (Control Run) | No. 66 (Test Run) | No. 67 (Test Run) | No. 68 (Test Run) | No. 69 (Test Run) | No. 70 (Control Run) |
|---|---|---|---|---|---|---|---|
| Oily Phase | Beeswax (parts) | 1.5 | 1.5 | 1.5 | 1.5 | 1.5 | 1.5 |
| | Cetanol (parts) | 2.0 | 2.0 | 2.0 | 2.0 | 2.0 | 2.0 |
| | Liquid Paraffin (parts) | 5.0 | 5.0 | 5.0 | 5.0 | 5.0 | 5.0 |
| | Isopropyl Palmitate (part) | 1.0 | 1.0 | 1.0 | 1.0 | 1.0 | 1.0 |
| Aqueous Phase | Basic Polypeptide-Stearic Acid Salt (parts)* | 2.33 (0.33) | 2.36 (0.36) | 2.45 (0.45) | 6.8 (4.8) | 11.3 (9.3) | 14.3 (12.3) |
| | Glycerol (parts) | 5.0 | 5.0 | 5.0 | 5.0 | 5.0 | 5.0 |
| | Methyl p-Hydroxybenzoate | Small amount | Small amount | Small amount | Small amount | Small amount | Small amount |
| | Deionized Water (parts) | 83.17 | 83.14 | 83.05 | 78.7 | 74.2 | 71.2 |
| Emulsion Stability (immediately after preparation) | | Poor | Good | Very good | Very good | Good | Rather poor |
| Storage Stability (45° C., 3 months) | | Poor | Good | Very good | Very good | Good | Poor |
| Appearance (texture and gloss) | | Rather poor | Good | Very good | Very good | Good | Rather poor |
| Feeling | | Rather poor | Good | Very good | Very good | Good | Rather poor |

*The amounts of the hydrous salts, together with those of the pure salts in parentheses, are indicated.

As can be seen from the data given in Table 18, the ratio of higher fatty acid (stearic acid) to basic polypeptide should be from 0.2 to 30 and preferably from 0.5 to 15.

EXAMPLE 13

(Massage Cream)

A mixture of 40 parts of liquid paraffin and 5 parts of stearic acid was melted by heating it to 80° C. To this melt was added an aqueous solution (at 80° C.) containing 5 parts of a basic polypeptide and a small amount of methyl p-hydroxybenzoate in 50 parts of water. The resulting mixture was emulsified by means of a homomixer and then cooled. When its temperature reached 30° C. a small amount of a perfume was added thereto and mixed therein. The massage cream thus obtained was found to be an O/W emulsion which presented an attractive appearance characterized by a fine texture, had a gloss value of 85, and gave a very good feeling. Moreover, when stored in a thermostatic chamber at 45° C. for 3 months, it showed no abnormality in its emulsified state and thus proved to be very excellent in emulsion stability and storage stability. The basic polypeptide used in this example was the basic polypeptide III described in Example 2.

EXAMPLE 14

(Cleansing Cream)

The procedure of Example 17 was repeated except that 55 parts of liquid paraffin, 10 parts of stearic acid, 28 parts of water, and 7 parts of a basic polypeptide were used. The cleansing cream thus obtained was found to be an O/W emulsion which presented an attractive appearance characterized by a fine texture, had a gloss value of 84, and gave a very good feeling. Moreover, when stored in a thermostatic chamber at 45° C. for 3 months, it showed no abnormality in its emulsified state and thus proved to be very excellent in emulsion stability and storage stability. The basic polypeptide used in this example was the basic polypeptide III described in Example 2.

EXAMPLE 15

(Skin Cream)

A mixture of 30 parts of squalane, 5 parts of microcrystalline wax, 2 parts of olive oil, and 5 parts of palmitic acid was melted by heating it to 80° C. To this melt was added an aqueous solution (at 80° C.) containing 4 parts of a basic polypeptide, 3 parts of glycerol, and small amount of methyl p-hydroxybenzoate in 51 parts of water. The resulting mixture was emulsified by means of a homomixer and then cooled. When its temperature reached 30° C., a small amount of a perfume was added thereto and mixed therein. The skin cream thus obtained was found to be an O/W emulsion which presented an attractive appearance characterized by a fine texture, had a gloss value of 86, and gave a very good feeling. Moreover, when stored in a thermostatic chamber at 45° C. for 3 months, it showed no abnormality in its emulsified state and thus proved to be excellent in emulsion stability and storage stability. The basic polypeptide used in this example was the basic polypeptide described in Example 2.

EXAMPLE 16

(Foundation Cream)

A mixture of 45 parts of liquid paraffin and 10 parts of stearic acid was melted by heating it to 80° C. On the other hand, 0.02 part of yellow iron oxide, 1.5 parts of titanium dioxide, 1.5 parts of kaolin, and 0.02 parts of red iron oxide were uniformly dispersed in an aqueous solution containing 8 parts of a basic polypeptide and a small amount of methyl p-hydroxybenzoate in 33.96 parts of water. This dispersion (at 80° C.) was added to the above melt (at 80° C.). The resulting mixture was emulsified and then cooled. When its temperature reached 30° C., a small amount of a perfume was added thereto and mixed therein. The foundation cream thus obtained was found to be an O/W emulsion which presented an attractive appearance and proved to be still stable after stored in a thermostatic chamber at 45° C. for 3 months. The basic polypeptide used in this example was the basic polypeptide III described in Example 2.

What is claimed is:

1. In a skin cosmetic composition which is an oil-in-water emulsion consisting essentially of from 25 to 90% by weight of water, as the continuous phase; from 0.5 to 60% by weight of cosmetic oil material, as the discontinuous phase, said oil material having no free carboxyl groups and being safe and effective for cosmetic use on the human skin; and an emulsifier in an amount effective to maintain in a stable condition the oil-in-water emulsion of said oil material in said water, the improvement which comprises: said emulsifier is selected from the group consisting of (a) a mixture of from 0.5 to 10% by weight of basic polypeptide, based on the total weight of said cosmetic composition, and higher fatty acid having from 12 to 22 carbon atoms, the amount of said higher fatty acid being from 0.2 to 30 times the amount of said basic polypeptide, said basic polypeptide consisting of a partial hydrolyzate of naturally occurring protein and having an average molecular weight of from 450 to 10,000, an isoelectric point of from 8.5 to 10.5 and an amino acid composition, derived from said naturally occurring protein, characterized by a ratio of basic amino acids to acidic amino acids in the range of from 1.05 to 3.0, and (b) from 1.0 to 20.0% by weight, based on the total weight of said cosmetic composition, of salt of said basic polypeptide and said higher fatty acid, wherein the amount of said higher fatty acid used to prepare said salt is from 0.2 to 30 times the weight of said basic polypeptide used to prepare said salt.

2. The cosmetic composition of claim 1, wherein said naturally occurring protein is selected from the group consisting of collagen, albumin, histone and protamine.

3. The cosmetic composition of claim 1, wherein said oil material is selected from the group consisting of liquid paraffin, squalane, petrolatum, ceresin, oliver oil, almond oil, avocado oil, castor oil, cocoa butter, palm oil, turtle oil, cod-liver oil, whale oil, beef tallow, butter fat, isopropyl myristate, isopropyl palmitate, butyl stearate, hexyl laurate, octyldodecyl myristate, di-isopropyl adipate, isocetyl myristate, di-isopropyl sebacate, beeswax, carnauba wax, spermaceti, lanolin, wool wax, solid paraffin, cetyl alcohol, oleyl alcohol, isostearyl alcohol and mixtures thereof.

4. The cosmetic composition of claim 1 wherein the basic polypeptide has an average molecular weight of from 1,000 to 5,000.

5. The cosmetic composition of claim 1 or claim 2 wherein the basic polypeptide has an amino acid composition characterized by a basic amino acid/acidic amino acid ratio of from 1.2 to 2.0.

6. The cosmetic composition of claim 1 or claim 2 wherein the basic polypeptide is used in an amount of from 1.0 to 8.0% by weight based on the total weight of the cosmetic composition.

7. The cosmetic composition of claim 1 or claim 2 wherein the higher fatty acid is used in an amount equal to from 0.5 to 15 times the amount of the basic polypeptide.

8. The cosmetic composition of claim 1 or claim 2 wherein said emulsifier is said salt and said salt is used in an amount of from 2 to 15% by weight, based on the total weight of the cosmetic composition.

9. The cosmetic composition of claim 1 wherein the higher fatty acid containing from 12 to 22 carbon atoms is selected from the group consisting of lauric acid, myristic acid, palmitic acid, stearic acid, oleic acid, isostearic acid, octyldecanoic acid, arachidonic acid and mixtures thereof.

10. The cosmetic composition of claim 1 wherein the amount of said water is from 30 to 80% by weight, based on the total weight of the cosmetic composition.

11. The cosmetic composition of claim 1 which further contains a pigment in an amount of not greater than 10% by weight, based on the total weight of the cosmetic composition.

12. The cosmetic composition of claim 11 wherein the pigment is at least one inorganic pigment selected from the group consisting of titanium dioxide, kaolin, yellow iron oxide, tri-iron tetroxide, and talc.

* * * * *

UNITED STATES PATENT AND TRADEMARK OFFICE
CERTIFICATE OF CORRECTION

PATENT NO. : 4 507 279

DATED : March 26, 1985

INVENTOR(S) : Genichiro Okuyama et al

It is certified that error appears in the above-identified patent and that said Letters Patent is hereby corrected as shown below:

Column 26, line 24; after "claim 1" insert ---or claim 2---.

*Signed and Sealed this*

*First* Day of *October 1985*

[SEAL]

*Attest:*

DONALD J. QUIGG

*Attesting Officer*

*Commissioner of Patents and Trademarks—Designate*